(12) United States Patent
Endou et al.

(10) Patent No.: US 9,618,512 B2
(45) Date of Patent: Apr. 11, 2017

(54) BIOMARKER FOR BREAST CANCER

(75) Inventors: Hitoshi Endou, Kanagawa (JP); Isao Okayasu, Tokyo (JP)

(73) Assignee: J-Pharma Co., Ltd., Kanagawa (JP)

( * ) Notice: Subject to any disclaimer, the term of this patent is extended or adjusted under 35 U.S.C. 154(b) by 137 days.

(21) Appl. No.: 14/111,401

(22) PCT Filed: Apr. 13, 2012

(86) PCT No.: PCT/JP2012/060114
§ 371 (c)(1),
(2), (4) Date: Dec. 18, 2013

(87) PCT Pub. No.: WO2012/141285
PCT Pub. Date: Oct. 18, 2012

(65) Prior Publication Data
US 2014/0106377 A1    Apr. 17, 2014

(30) Foreign Application Priority Data
Apr. 15, 2011  (JP) .................................. 2011-091378

(51) Int. Cl.
*G01N 33/574* (2006.01)
*C07K 16/28* (2006.01)
(52) U.S. Cl.
CPC ....... *G01N 33/57415* (2013.01); *C07K 16/28* (2013.01)
(58) Field of Classification Search
None
See application file for complete search history.

(56) References Cited

U.S. PATENT DOCUMENTS

| | | |
|---|---|---|
| 5,698,410 A | 12/1997 | Burstein et al. |
| 2003/0148444 A1 | 8/2003 | Endou et al. |
| 2003/0157548 A1 | 8/2003 | Nawa et al. |
| 2005/0003490 A1 | 1/2005 | Endou et al. |
| 2009/0155798 A1* | 6/2009 | Ring ................ C12Q 1/6886 435/6.16 |

FOREIGN PATENT DOCUMENTS

| | | |
|---|---|---|
| EP | 1111048 A2 | 6/2001 |
| EP | 2146208 A1 | 1/2010 |
| JP | H11-511245 A | 9/1999 |
| JP | 2000-157286 A | 6/2000 |
| JP | 2000-342270 A | 12/2000 |
| JP | 2001-046070 A | 2/2001 |
| JP | 2001-211886 A | 8/2001 |
| JP | 2001-228146 A | 8/2001 |
| JP | 11-511245 A | 9/2001 |
| JP | 2001-245661 A | 9/2001 |
| JP | 2011-024537 A | 2/2011 |

OTHER PUBLICATIONS

Bartlett et al. (Breast Cancer Research, 2010, 12:R47 pp. 1-11).*
Verry et al. (European Journal of Physiology, 2004, 447:532-542).*
Bloom et al. (Cancer Research, 2012, 72:P2-10-04).*
Ring et al. (Journal of Clinical Oncology, 2006, 24:3039-3047; appendix pp. 6-14).*
Official Action issued Nov. 15, 2014, by the State Intellectual Property Office of the People's Republic of China in related Chinese Patent Application No. CN 201280023071.2, with English machine-translation (14 pages).
Extended European Search Report dated Oct. 24, 2014, issued by the European Patent Office in corresponding European Patent Application No. 12770851.9 (7 pages).
Segawa, Hiroko, et al., "Identification and Functional Characterization of a Na+-independent Neutral Amino Acid Transporter with Broad Substrate Selectivity"; The Journal of Biological Chemistry, vol. 274, No. 28, Issue of Jul. 9, 1999; pp. 19745-19751.
Sakata, Takeshi, et al., "L-type amino-acid transporter 1 as a novel biomarker for high-grade malignancy in prostate cancer"; Pathology International, vol. 59 (2009); doi: 10.1111/j.1440-1827.2008.02319. x; p. 7-18.
Ichinoe, Masaaki, et al., "High expression of L-type amino-acid transporter 1 (LAT1) in gastric carcinomas: Comparison with non-cancerous lesions"; Pathology International, vol. 61 (2011); doi: 10.1111/j.1440-1827.2011.02650.x; pp. 281-289.
Liedtke, Cornelia, et al., "Response to Neoadjuvant Therapy and Long-Term Survival in Patients With Triple-Negative Breast Cancer"; Journal of Clinical Oncology, vol. 26, No. 8, Mar. 10, 2008; pp. 1275-1281.
International Search Report mailed Jul. 3, 2012, by the Japan Patent Office in related International Application No. PCT/JP2012/060114, with English translation (6 pages).
International Search Report mailed Jul. 3, 2012, issued by the Japan Patent Office, in related International Application No. PCT/JP2012/060114, with English translation (6 pages).
English translation of an International Preliminary Report on Patentability (IPRP) and Written Opinion dated Oct. 15, 2013, issued by the International Bureau of WIPO, in related International Application No. PCT/JP2012/060114 (8 pages).
Uchigasaki, Shin'ya, et al., "L-type amino acid transporter 1 (LAT1); Histopathological and immunohistochemical studies on L-type amino acid transporter 1 (LAT1) expression for breast tumors"; Japanese Journal of Diagnostic Pathology, vol. 19, No. 3, Jul. 31, 2002 (Jul. 31, 2002); pp. 189 to 194, with English Abstract (1 page).
Sasaki, Yuka, et al., "Bunshi Hyoteki Chiryo to Byori Nyugan to Bunshi Hyoteki Chiryo"; Pathology and clinical Medicine, vol. 24, No. 6, Jun. 1, 2006 (Jun. 1, 2006); pp. 625-633, with English Abstract (1 page).

(Continued)

*Primary Examiner* — Julie Wu
(74) *Attorney, Agent, or Firm* — Osha Liang LLP (57) ABSTRACT

A method for the diagnosis of breast cancer using an anti-LAT1 monoclonal antibody. Among intraductal breast neoplastic lesions, duct carcinoma in situ, which is malignant, expresses LAT1 at a significantly high level, as compared to intraductal breast papilloma, which is benign. An anti-LAT1 monoclonal antibody is useful for the discrimination between these two lesions. Further, LAT1 is expressed at a high level in most of triple negative infiltrating carcinomas, which are negative for all of ER, PgR, and HER2 that are conventional molecular targeting markers for breast cancer. Therefore, LAT1 can be used as a novel molecular targeting marker for the triple negative breast cancer.

4 Claims, 3 Drawing Sheets

(56) References Cited

OTHER PUBLICATIONS

Nakamura, Harumi, et al., "VIII Byori Saiboshin 3 I Nyugan"; Modern Medical Laboratory, vol. 38, No. 10, Sep. 15, 2010 (Sep. 15, 2010); pp. 1003-1008, with English Abstract (1 page).

Kanai, Yoshikatsu, et al., "Expression Cloning and Characterization of a Transporter for Large Neutral Amino Acids Activated by the Heavy Chain of 4F2 Antigen (CD98)"; The Journal of Biological Chemistry, vol. 273, No. 37, Sep. 11, 1998; pp. 23629-23632.

Iwase, Hirotaka, et. al., "Clinicopathological analyses of triple negative breast cancer using surveillance data from the Registration Committee of the Japanese Breast Cancer Society"; Brease Cancer, vol. 17 (2010); DOI: 10.1007/s12282-009-0113-0; pp. 118-124.

Sinicrope, Frank A., et al., "bcl-2 and p53 Oncoprotein Expression during Colorectal Tumorigenesis";Cancer Research, vol. 55, Jan. 15, 1995; pp. 237-241.

Yanagida, Osamu, et al., "Human L-type amino acid transporter 1 (LAT1): characterization of function and expression in tumor cell lines"; Biochimica et Biophysica Acta, vol. 1514 (2001); pp. 291-302.

Segawa, Hiroko, et al., "Identification and Functional Characterization of a Na+- independent Neutral Amino Acid Transporter with Broad Substrate Selectivity"; The Journal of Biological Chemistry, vol. 274, No. 28, Issue of Jul. 9, 1999; pp. 19745-19751.

Sakata, Takeshi, et al., "L-type amino-acid transporter 1 as a novel biomarker for high-grade malignancy in prostate cancer"; Pathology International, vol. 59 (2009); doi: 10.1111/J.1440-1827.2008.02319.x; pp. 7-18.

Ichinoe, Masaaki, et al., "High expression of L-type amino-acid transporter 1 (LAT1) in gastric carcinomas: Comparison with non-cancerous lesions"; Pathology International, vol. 61 (2011); doi: 10.1111/1440-1827.2011.02650.x; pp. 281-289.

Oda, Koji, et al., "L-Type amino acid transporter 1 inhibitors inhibit tumor cell growth"; Cancer Science, Journal of the Japanese Cancer Association, vol. 101, No. 1, Jan. 2010; doi: 10.1111/j.1349-7006.2009.01386.x; pp. 173-179.

Rakha, Emad A., et al., "Prognostic Markers in Triple-Negative Breast Cancer"; American Cancer Society, vol. 109, No. 1, Jan. 1, 2007; DOI: 10.1002/cncr.22381; pp. 25-32.

Liedtke, Cornelia, et al., "Response to Neoadjuvant Therapy and Long-Term Survival in Patients With Triple-Negative Breast Cancer"; Journal of Clinical Oncology, vol. 26, No. 8, Mar. 10, 2008; pp. 1275-1281.

Sasaki, Yuka, et al., "Clinicopathological characteristics of triple-negative breast cancers"; The Japanese Breast Cancer Society 2009 Symposium: Triple negative breast cancer; Breast Cancer, vol. 16 (2009); DOI: 10.107/s12282-009-0153-5; pp. 254-259.

* cited by examiner

BIOMARKER FOR BREAST CANCER

CROSS REFERENCE TO RELATED APPLICATIONS

This is a national stage application based on PCT/JP2012/060114, filed on Apr. 13, 2012, which claims priority to Japanese Patent Application No. 2011-091378, filed on Apr. 15, 2011. This application claims the priority of these prior applications and incorporates their disclosures by reference in their entireties.

TECHNICAL FIELD

The present invention relates to a biomarker for breast cancers, specifically to a kit and a method for the diagnosis of mammary gland tumors.

BACKGROUND ART

A neutral amino acid transporter [L-type amino acid transporter (LAT)] is a transmembrane-type protein which engages in cellular uptake of neutral amino acids such as glycine, alanine, leucine, isoleucine, valine, serine, threonine, cysteine, asparagine, glutamine, methionine, phenylalanine, tyrosine, tryptophan, histidine, L-DOPA, and the like. The present inventors have been searching various LATs and have found LAT1 and isoforms thereof, namely, LAT2, LAT3, and LAT4.

Among them, LAT1 is a 12-pass transmembrane spanning domain protein that has the ability to transport large neutral amino acids such as leucine, isoleucine, valine, methionine, phenylalanine, tyrosine, tryptophan, histidine, and the like; and L-DOPA, $Na^+$ coexisting with an amino-acid transport activating factor, 4F2hc independently. Moreover, LAT1 is mainly expressed in vivo such as in placenta, spleen, colon, testis, and a blood-brain barrier. Also, the expression of LAT1 is recognized in a human signet ring cell carcinoma cell line, a small cell lung cancer cell line, a melanoma cell line, a neuroblastoma cell line, and further confirmed by immunohistochemical staining in tumor tissues of kidney cancers, bladder cancers and prostate cancers (refer to Patent Literature 1, Non-Patent Literature 1 and Non-Patent Literature 2). The suppression of the expression of LAT1 by suppressors such as melphalan, BCH, and the like remarkably reduces the growth rate of cultured cells that are expressing LAT1. Therefore, the intracellular uptake of essential amino acids by LAT1 is absolutely imperative for cell proliferation, and it has been thought that the expression of LAT1 at a high level helps cancer cells to obtain a superior nutrition state compared to normal cells, so cancer cells are predominant in cell proliferation over normal cells.

LAT2, which is the isoform of LAT, has a transmembrane structure that spans the intracellular membrane 12 times as well as LAT1, and has a substrate selectivity in a broad range that allows a $Na^+$ independent transport of all the neutral amino acids, including small amino acids such as glycine, alanine, serine, threonine, cysteine, asparagine, and glutamine in addition to large amino acids, by coexisting with 4F2hc. It has been confirmed that LAT2 is expressed in normal tissues in the brain, skeletal muscles, kidney, jejunum, ileum, testis, and placenta, but not in tumor tissues (refer to Patent Literature 2 and Non-Patent Literature 3). Since the affinity of LAT2 with a substrate is low compared to that of LAT1, LAT2 is thought to play a role in transporting neutral amino acids in cells of normal tissues that do not require active cell proliferation.

Furthermore, the present inventors have found various transporters including a sodium independent small neutral amino acid transporter that transports L- and D-forms amino acids (refer to Patent Literature 3), and also a transporter of which substrates are cystine, basic amino acids, and neutral amino acids (refer to Patent Literature 4). A transporter is defined as a transmembrane-type protein having a function of taking up various substances that are essential to cells in a substance-specific way, so it is essential for the maintenance and proliferation of body tissues. Therefore, many methods for the diagnosis of diseases by utilizing various transporters have been proposed. For example, methods including one to detect the presence or absence of the expression of a protein or to determine the amount of the protein in samples derived from organs or the part of thereof containing tumor cells, tumor tissues, or tumors (refer to Patent Literature 1); a method for the diagnosis of lung/thoracic diseases characterized by using the antibody of an anion transporter (refer to Patent Literature 5); a method to diagnose whether patients are affected in integration disorder syndrome by a quantitative value of a protein, a fragment thereof, or nucleic acid of an erythrocyte urea transporter as an index (refer to Patent Literature 6); a method for discriminating benignancy from malignant tumor overexpressed GLUT-1 by preparing a cytological preparation from body cavity fluid and comparing the expression level of GLUT-1 to a tissue sample obtained from the section of non-malignant tissues of the same type of tissues using an antibody that can bind to the transmembrane glucose transporter GLUT-1 (refer to Patent Literature 7) have been reported.

Mainly three biomarkers intended for use in the treatment of breast cancer are known, that is, estrogen receptor (ER), progesterone receptor (PgR) and HER2 (a receptor of growth factor, which is also referred to as EGFR2). In case an immunohistochemistry or FISH method is carried out for each biomarker in tumor tissues and finds positive cases, the treatment method targeted to a corresponding biomarker has been chosen for cases showing positive to each biomarker. On the other hand, a breast cancer that shows negative for all of these markers (three proteins, these are an estrogen hormone receptor, progesterone hormone receptor and HER2 are not expressed in tumor cells in cancer) is referred to as triple negative breast cancer, which accounts for 12 to 25% of the total population of breast cancer cases (refer to Non-Patent Literature 7 to 10). Appropriate treatment method for the triple negative breast cancer has not been developed still now. The patients have poor prognosis compared to those to breast cancer that show positive to either of three markers (refer to Non-Patent Literature 9 and 10).

Also, a histopathology method using specimens stained with conventional HE (hematoxylin-eosin) is carried out for the discrimination between malignant ductal carcinoma in situ (hereinafter sometimes referred to as DCIS) and benign intraductal breast papilloma (intraductal breast papilloma) in intraductal breast tumors. However, well-defined discrimination elements are not clear, so there are many lesions that are difficult to discriminate between benignancy and malignancy. Therefore, the development of a marker that can provide more explicit discrimination is needed.

CITATION LIST

Patent Literature

Patent Literature 1: JP 2000-157286 A
Patent Literature 2: JP 2000-342270 A

Patent Literature 3: JP 2001-211886 A
Patent Literature 4: JP 2001-46070 A
Patent Literature 5: JP 2001-228146 A
Patent Literature 6: JP 2001-245661 A
Patent Literature 7: JP 11-511245 W Non-Patent Literature Non-Patent Literature 1: Kanai, Y., et al., J. Biol. Chem., 273, 23629-23632, 1998
Non-Patent Literature 2: Yanagida O., et al., Biochim. Biophys. Acta., 1514(2), 291-302, 2001
Non-Patent Literature 3: Segawa, H., et al., J. Biol. Chem., 274(28), 19745-19751, 1999
Non-Patent Literature 4: Sakata T., et al., Pathol. Int. 59, 7-18, 2009
Non-Patent Literature 5: Ichinohe M., et al., Pathol. Int., 2011 in press
Non-Patent Literature 6: Oda K., et al., Cancer Sci., 101, 173-179, 2010
Non-Patent Literature 7: Rakha E. A., et al., Cancer 109, 25-32, 2007
Non-Patent Literature 8: Liedtke C., et al., J. Clin. Oncol. 26, 1275-1281, 2008
Non-Patent Literature 9: Sasaki Y., et al., Breast Cancer 16, 254-259, 2009
Non-Patent Literature 10: Iwase H., et al., Breast Cancer 17, 118-124, 2010
Non-Patent Literature 11: Sinicrope F. A., et al., Cancer Res. 55, 237-241, 1995

SUMMARY OF INVENTION

Technical Problem

The present invention provides a method and a kit for the diagnosis of mammary gland tumors. More specifically, first, the present invention relates to a kit and a method for the diagnosis of triple negative breast cancer that is negative for all of ER, PgR and HER2. Second, the present invention relates to a kit and a method for the diagnosis of the degree of malignancy of intraductal breast tumors, which were conventionally difficult to discriminate by simple methods.

Solution to Problem

The present inventors have focused on and have researched a cancer-type of amino acid transporter that was specifically harnessed by cancer cells, aiming at the development of a molecular-targeted therapy for cancer. LAT2 was mainly used for the study of normal cells and LAT1, which has the efficient uptake ability of amino acids, was used for the study of cancer cells. The present inventors produced a mouse monoclonal antibody against LAT1, and developed an immunohistological research method by utilizing this antibody (refer to Non-Patent Literature 4). The inventors have found that cases showing the expression of LAT1 at a high level in patients with prostate cancer and gastric cancer had a significantly poor prognosis compared to cases expressing LAT1 at a low level by using this method (refer to Non-Patent Literature 4 and 5). Furthermore, the inventors have also developed a cancer therapy that integrates diagnosis and treatment as well as the development of LAT1 specific suppressive substances (refer to Non-Patent Literatures 4 to 6).

The present inventors have extensively studied the expression of LAT1 in intraductal breast tumor by an immunohistological technique using the anti-LAT1 monoclonal antibody aiming at the goal of establishing a molecular-targeted therapy whose target is this LAT1 in breast cancer, based on a finding that LAT1 is expressed in cancer at a high level with efficient uptake of amino acids to promote proliferation of cancer cells as mentioned above. As a result, the inventors have found that the expression of LAT1 in ductal carcinoma in situ is high compared to intraductal breast papilloma, and an immunostaining method is useful for the discrimination between benignancy and malignancy of intraductal breast tumors.

Furthermore, the inventors found that the usage of anti-LAT1 monoclonal antibodies in triple negative breast cancer tissues, which are negative for all of ER, PgR, and HER2, revealed the expression of LAT1 at a high level in 14 out of 17 cases.

Thus, the present inventors have found that LAT1, which is a transporter for essential amino acids specifically in kidney or bladder cancer, and LAT2, which is found in normal cells. Surprisingly, the present inventors found that employing the anti-LAT1 monoclonal antibody enables the discrimination between malignancy and benignancy in intraductal breast tumor and that LAT1 was expressed in so-called triple negative breast cancer tissues with a high probability.

The present invention (1) relates to a kit for diagnosis including an anti-LAT1 monoclonal antibody for detecting, identifying, or quantifying LAT1 for the diagnosis of mammary gland tumor.

The present invention (2) relates to the kit for diagnosis according to the preceding clause (1), wherein the mammary gland tumor is intraductal breast tumor and the degree of malignancy in the mammary gland tumor is diagnosed.

The present invention (3) relates to the kit for diagnosis according to the preceding clause (1), wherein the mammary gland tumor is triple negative breast cancer that is negative for all of estrogen receptor, progesterone receptor and HER2.

The present invention (4) relates to a kit for diagnosis of mammary gland tumors including the combination of an immunostaining kit of estrogen receptor, an immunostaining kit of progesterone receptor and an immunostaining kit of HER2, and an immunostaining kit of LAT1.

The present invention (5) relates to a method for the diagnosis of mammary gland tumors including the steps of detecting, identifying, or quantifying LAT1 in the tissue by contacting the anti-LAT1 monoclonal antibody with mammary gland tissues extracted from subjects.

The present invention (6) relates to the method according to the preceding clause (5), wherein the mammary gland tumors are intraductal breast tumors and include the diagnosis of the degree of malignancy thereof.

The present invention (7) relates to the method of diagnosis according to the preceding clause (5), wherein the mammary gland tumor is triple negative breast cancer that is negative for all of estrogen receptor, progesterone receptor, and HER2.

The present invention (8) is a method for the diagnosis of mammary gland tumor including an immunostaining of estrogen receptor, an immunostaining of progesterone receptor, an immunostaining of HER2 and LAT1.

Advantageous Effects of Invention

According to the clauses (1) and (5) in the present invention, diagnosis can be easily conducted to show guidelines for the treatment of mammary gland tumors, which was difficult to do until now. More specifically, the examination of LAT1 expression in breast cancer by immunostaining using the anti-LAT1 antibody of mammary gland tumors enables conducting an effective cancer therapy for breast cancers of which the target is LAT1.

According to the clauses (2) and (6) in the present invention, the discrimination between benignancy (intraductal breast papilloma) and malignancy of intraductal breast tumors (ductal carcinoma in situ) can be easily conducted, of which diagnosis was difficult.

According to the clauses (3) and (7) in the present invention, most triple negative breast cancers that are negative for all of ER, PrG, and HER2 have a poor prognosis, but, guidelines for the treatment for triple negative breast cancer can be provided.

According to the clauses (4) and (8) in the present invention, highly accurate guidelines of the treatment can be provided in diagnosing breast cancer by the combined usage of an anti-LAT1 monoclonal antibody with ER, PgR and HER2 that have been conventionally known as markers.

In the present invention, mammary gland tumors are not particularly limited as long as mammary gland tissues contain tumors. Typical examples include, for example, benign tumors such as intraductal breast papilloma, adenoma of the nipple, and the like; malignant tumors such as noninfiltrating cancers (ductal carcinoma in situ, and the like), infiltrating carcinomas [ductal carcinoma in situ (papillotubular carcinoma, solid-tubular carcinoma, scirrhous carcinoma), specific type], Paget's disease, and the like. Moreover, mammary gland tumors are divided into breast cancer, which is malignant tumor, and benign tumors according to another classification.

The intraductal breast tumors are not particularly limited as long as tumors are contained inside of breast ducts Typical examples include, for example, intraductal breast papilloma (benign tumor) and ductal carcinoma in situ (malignant tumor).

DESCRIPTION OF EMBODIMENTS

The LAT used in the present invention is a functional protein having the ability of cellular membrane transport of essential amino acids that are prerequisite for cellular proliferation, especially LAT specifically expressed in cancer cells is a functional protein that is identical in the function of cellular membrane transport of essential amino acids, which proves the growth of cancer cells. Therefore, the method disclosed in the present invention using more than two LAT including these different types of LAT permits not only the assessment of the presence or absence of cancer but also the accurate evaluation of the degrees of the malignancy in cancer.

One of the characteristics of the present invention is that the examination of LAT1 expression in breast cancer by immunostaining using the anti-LAT1 antibody of mammary gland tumors enables conducting an effective cancer therapy for breast cancers of which the target is LAT1.

In the present invention, LAT that is expressed in normal cells includes, for example, LAT2. Moreover, LAT that is expressed in tumor cells in the present invention includes, for example, LAT1.

Samples in the present invention include, for example, mammary gland tumor cells of mammals including human. In the present invention, a method is not particularly limited as long as methods can detect, identify, or quantify LAT in samples, a preferable method includes a method to use the antibody of LAT. As the antibodies of LAT, as long as being an antibody having reactivity to the total or partial length of the LAT protein and specificity to LAT, there is not particularly limited though.

The antibody in the present invention can be produced according to the production methods of antibodies that are publicly known. Specifically, the antibody against LAT in the present invention may be any of the following; a natural type of antibody that is produced by immunizing with LAT or the part of LAT in the present invention (including a natural form, a recombinant form, a chemical compound) or cells expressing the protein as an immunogenic agent to non-human mammals such as mice, rats, hamsters, guinea-pigs, chickens, rabbits, goats, and sheep to obtain a natural-type antibody according to a common procedure; a recombinant chimera monoclonal antibody and recombinant human-type monoclonal antibody that is produced using a genetic recombination technology (CDR-grafted antibody); and a human-type antibody that is produced using transgenic animals and the like. A monoclonal antibody also includes monoclonal antibodies having any isotypes of IgG, IgM, IgA, IgD, and IgE. Preferably, the isotype of the monoclonal antibody is IgG or IgM.

In case the antibody of the present invention is used, it is preferable to be labeled, or used with a modification that can be labeled in order to the result obtained in the study using the antibody that can be detected, identified, or quantified as signals. The labeled antibody of the present invention includes an antibody that is labeled with an enzyme, a fluorescent substance, a chemiluminescent substance, biotin, avidin or radioisotope such as $^3$H, $^{14}$C, $^{125}$I, or an antibody that has a binding ability with such labeled substances.

A "labeling substance that enables obtaining detectable signals by alone or reacting with other materials" for labeling the antibody in the present invention means a substance that is used for converting the presence of the monoclonal antibody to be a detectable signal by binding it to the above mentioned antibody physically or chemically. Specifically, such a substance includes an enzyme, a fluorescent substance, a chemiluminescent substance, biotin, avidin, the radioisotope, or the like. Specifically, examples include enzymes such as peroxidase [for example, horseradish peroxidase etc.], alkaline phosphatase, β-D-galactosidase, glucose oxidase, glucose-6-phosphate dehydrogenase, alcohol dehydrogenase, malate dehydrogenase, penicillinase, catalase, apoglucose oxidase, urease, luciferase, or acetylcholinesterase, and the like; fluorescent substances such as fluorescein isothiocyanate, phycobiliprotein, rare-earth metal chelate, dansyl chloride, tetramethylrhodamine isothiocyanate, and the like; radioisotopes such as $^3$H, $^{14}$C, $^{125}$I, and the like; biotin, avidin, or chemiluminescent substances.

Herein, radioisotopes and fluorescent substances can independently radiate detectable signals. However, enzymes, chemiluminescent substances, biotin, or avidin alone cannot radiate detectable signals as they are. Detectable signals can be obtained by reacting with one or more other substances. For example, in case an enzyme is used, at least a substrate is necessary to get detectable signals. For this purpose, various substrates are used depending on the methods of measuring enzyme activities (a colorimetric method, a fluorescence method, a bioluminescence method or a chemiluminescence method, and the like). For example, in case peroxidase is used, hydrogen peroxide is used as a substrate. Moreover, in case biotin is used, at least avidin or enzyme-modified avidin (for example, streptavidin-β-galactosidase) is generally reacted as a substrate but not limited to this. Furthermore, various chromogenic substances are used depending on the substrate when needed. For example, in case streptavidin-β-galactosidase is used as a substrate for biotin, 4-methyl-umbelliferyl-β-D-galactoside can be used as a chromogenic substance.

The labeled antibody in the present invention can be used for detecting, identifying, or quantifying LAT in the present invention, and measurement methods for this purpose can be conducted using widely available immunohistological techniques according to a common procedure (for example, refer to Experimental Medicine Supplemental volume, "Cell engineering Handbook", Yodosha Co. Ltd., pp. 0.201-213, 1992). Moreover, the labeled antibody of the present invention can be employed not only for the immunohistological test, but also for a western blotting method, which includes preparing a soluble membrane protein from cells, tissues or organs in samples, or the part thereof according to a common procedure, and confirming the presence or absence of LAT of the present invention in the soluble membrane protein by reacting the labeled antibody with the soluble membrane protein. In the immunologic measurement method, the antibody labeled with any labeling substances mentioned above can be used, a monoclonal antibody labeled with an enzyme such as peroxidase and the like, or labeled with biotin is preferably used in light of the detection sensitivity and qualification sensitivity at the high degree or the convenience of handling.

A method for detecting, identifying, or quantifying LAT in the present invention can be conducted by the immunohistological technique and the like. Specifically, for example, methods containing the following processes (1) and (2) can be recited.
(1) A process of contacting the labeled anti-LAT antibody of the present invention with a sample; and
(2) A process of measuring the labeled antibody bound to LAT in the sample by detecting the intensities of fluorescence, chemiluminescence, or radioactivities depending on the types of the labeling substances bound to the antibody.

More specifically, for example, the following processes can be included.
(Process 1) A process to prepare a fixed sample that is extracted from a test sample, and fixed with paraformaldehyde and the like;
(Process 2) A process to subject to the fixed sample to an antigen-antibody reaction by addition of the labeled antibody in the present invention, which is labeled with an enzyme such as biotin or peroxidase;
(Process 3) A process of adding various substrates, avidin or enzyme-modified avidin such as streptavidin-β-galactosidase, and the like depending on the types of the enzymes used, and further reacting the substrate, avidin or enzyme-modified avidin with the labeling substance of the labeled antibody after washing the fixed sample when needed;
(Process 4) A process of adding various substrates (for example, 4-methyl-umbelliferyl-β-D-galactoside, and the like) depending on the types of the enzymes for the modification, and reacting the enzyme bound to avidin with the substrate in case enzyme-modified avidin is added in Process 3;
(Process 5) A process of washing the fixed sample when needed, and stopping the enzyme reaction and chromogenic reaction; and
(Process 6) A process of measuring colorimetric intensities, fluorescence intensities or luminescent intensities through the observation of the fixed sample under microscopy.

The method for detecting, identifying, or quantifying in the present invention is further explained in detail by the example of the detecting method for cancer cells in mammary gland tissues using an immunostaining technique. The method of the present invention is one that detects cancer cells or fragments thereof in mammary gland tissues, and diagnoses the degree of their malignancy. Since the method of the present invention can provide direct visual observation of the presence or absence of LAT1 by immunostaining, the assessment of either negative or positive for the sample can be carried out in a simple and certain manner without special skills.

Special examples of the method for detecting, identifying, or quantifying in the present invention include, for example, the following methods described in (1) to (4) but not particularly limited to these.

(1) Detection of Cancer Cells by Tissues and a Smear Method

An extracted tissue was subjected to formalin fixation and paraffin embedding, and then a tissue section of 3 μm in thickness is prepared and placed it on a slide glass. After deparaffinizing this section, it is independently treated with anti-LAT1 and LAT2 antibodies that can specifically bind to an amino acid transporter (treatment of a primary antibody). After treating with the primary antibody, the sample is independently treated with a secondary antibody, which can specifically bind to the primary antibody, labeled with an enzyme or fluorescence dye such as DAB (3,3'-diaminobenzidine tetrahydrochloride), methyl green, Mayer's Hematoxylin, and the like (treatment of secondary labeled antibody). When the secondary antibody labeled with an enzyme is used, a substrate solution is added, subsequently the reaction mixture produces color, and is then assessed either positive or negative by the observation of cells using a light microscope. When the secondary antibody labeled with fluorescence dye is used, the presence or absence of cancer cells is assessed after the treatment of the secondary antibody by observation with a fluorescence microscope. In the smear method, the extracted cell is coated on the glass as it is or it is separated into a cell component and a liquid component with a centrifuge and then the cell component (sediment) is subjected to immunostaining. That is, the sediment is coated on the slide glass, and then is fixed with an ethanol solution or a 10% formalin solution. Subsequently the tissue section is subjected to immunostaining and evaluated.

(2) Detection of Cancer Cell by a Cryoembedding Method

The extracted tissue is rapidly frozen with liquid nitrogen after embedding with an OCT Compound, and then a slide specimen is prepared by thinly slicing with a cryostat. This specimen is fixed with 10% formalin or an ethanol solution and the like, and then is subjected to immunostaining in the method described in (1). In case the extracted cells are used, the cells are separated with a centrifuge and the resultant sediment component is fixed with 10% formalin, and then cells are re-centrifuged with discarding the supernatant to obtain a cell component. To the cell component is added 2% agarose (50 µL) while warming with a heat block and mixing. Subsequently, the cell is fixed at a temperature of 4° C. and the sediment component is encapsulated in a gel. The solidified gel is embedded with an OCT Compound, from which a frozen block is prepared, a slide specimen is prepared by thinly slicing the frozen block with a cryostat. The cells on the slide specimen are treated according to a common method and stained with fluorescence immunohistochemistry. The specimen after staining is viewed under a fluorescence microscope to assess the presence or absence of cancer cells.

(3) Detection of Cancer Cells by a Paraffin Embedding Method of the Extracted Cell The gel embedded in the sediment is treated by the following method depending on the situation, and the assessment of the presence or absence of cancer cells using the paraffin specimen can also be carried out. The gel is treated with 4% formalin at a temperature of 4° C. overnight, and then is washed with PBS. Subsequently is subjected to dehydration and penetration according to a conventional method. After penetration, the gel is embedded with paraffin and a paraffin block is prepared. The prepared block is thinly sliced with a microtome, and a slide specimen is prepared. The prepared slide specimen is subjected to deparaffinization treatment according to a conventional method, and then fluorescence immunohistochemistry is carried out. Subsequently, the specimen is viewed under a fluorescence microscope and the presence or absence of cancer cells is assessed. Breast cancer tissues can be detected by the method of the present invention using immunohistochemistry technique and the like.

(4) Detection of Cancer Cells by a Method of Using ELISA

The protein levels of LAT in the extracted tissue can be quantified by the detection of LAT protein present in the extracted tissue by an ELISA method, thus more quantitative assessment becomes feasible. The sample is treated with surfactant and ultrasound, and is separated with an ultracentrigufe at a temperature of 4° C. at 100,000×g to obtain a protein pellet with discarding the supernatant. The pellet is added 10% BSA/PBST in an appropriate amount and suspended by the treatment of ultrasound. This is used as a sample and an ELISA method is carried out.

First, the sample is added to an immunoplate at a concentration of 100 µL/well and left it at a temperature of 4° C. overnight. The sample solution is discarded and a blocking solution is added, and then the plate is left at room temperature for 1 hour. The blocking solution in the well is discarded and an appropriately diluted anti-LAT primary antibody solution is added, and then the plate is left at room temperature for 2 hours (during this reaction, the anti-LAT antibody binds to LAT protein coated on the on the bottom of the well independently). The primary antibody is discarded and is washed with PBST, and then an arbitrarily diluted labeled secondary antibody is added, and the plate is left at room temperature for 1 hour. The inside of the well is washed with PBST and a substrate solution is added to produce color or chemiluminescence. The presence or absence of LAT protein is confirmed and assessed by measuring the amounts of dye or the intensities of luminescence with a spectrophotometer or luminometer.

The other characteristic of the present invention is that the degrees of malignancy of tumors in intraductal breast tumor tissues can be assessed. The method of assessing the degrees of malignancy of tumors in intraductal breast tumors in the sample of the present invention includes the quantitative measurement of the LAT. That is, the amount of normal cells can be obtained by quantifying LAT expressed in normal cells, and the amount of tumor cells can be also obtained by quantifying LAT expressed in tumor cells. Furthermore, these cells require the same type of LAT; therefore the quantitative values of both cells can indicate the percentage of the cells become tumor cells. Therefore, the present invention also provides a method of assessing the degree of malignancy of tumor cells of the sample including quantifying LAT2 expressed in normal cells; quantifying LAT1 expressed in tumor cells; and comparing the quantitative values of both cells.

The other characteristic of the present invention is that it can provide a treatment guideline for mammary gland tumor, wherein the mammary gland tumor is triple negative breast cancer that is negative for all of estrogen receptor, progesterone receptor, and HER2. Since most triple negative breast cancers express LAT1 at a high level, it is found that the treatment targeting LAT1 is effective for triple negative breast cancer for which there is no proper treatment until now. Moreover, whether general breast cancer is triple negative or not, the treatment targeting LAT1 is effective by testing the presence or absence of the expression of LAT1.

Another characteristic of the present invention is that the diagnosis for breast cancer can be feasible by combining an immunostaining of ER (estrogen receptor), an immunostaining of PgR (progesterone receptor), an immunostaining of HER2, and an immunostaining of LAT1. In the present invention, diagnosis for breast cancer can be conducted more precisely by the immunostaining of LAT1 using the anti-LAT1 monoclonal antibody in addition to the immunostaining using ER, PgR and HER2. Commercially available materials can be used for the immunostaining of ER, PgR and HER2. For example, a Ventana XT system (Ventana Japan, Tokyo, Japan) can be used for the immunostaining of ER and PgR; furthermore, a DAKO EGER pharm Dx kit (Dako North America Inc., Carpinteria, Calif., USA) can be used as the immunostaining kit for HER2. However, it is not limited to these as long as means can measure ER, PgR and HER2. In case estrogen, progesterone or analogs of these hormones are used, the effect of hormonal therapy can be estimated by evaluating the presence or absence of the expression of ER and PgR. The effect of anti-HER2 pharmaceutical agents in breast cancer can be estimated by evaluating the presence or absence of the expression HER2 gene. Similar to these, the effect of LAT1 transporter regulatory agents can be estimated by evaluating the presence or absence of the expression LAT1 by an immunostaining kit of LAT1 using the anti-LAT1 monoclonal antibody. This immunostaining may be conducted at the same time or independently.

(Kit)

Furthermore, the present invention provides a diagnostic kit for conducting any of each method in the present invention previously mentioned. That is, the present invention relates to a kit for diagnosis including an anti-LAT1 monoclonal antibody to detect, identify, or quantify LAT1 for the diagnosis of mammary gland tumors. Such a diagnostic kit may be one for diagnosing the degrees of the malignancy in mammary gland tumor, wherein mammary gland tumor is intraductal breast tumor, or triple negative breast cancer that is negative for all of estrogen receptor, progesterone receptor and HER2. Moreover, the present invention relates to a kit for diagnosis of mammary gland tumor including the combination of an immunostaining kit of estrogen receptor, an immunostaining kit of progesterone receptor and an immunostaining kit of HER2 and an immunostaining kit of LAT1. Also, the present invention relates to a kit to identify the expression of LAT1 whether the test result of estrogen receptor, progesterone receptor and HER2 in mammary gland tumors is either positive or negative.

In detail, the present invention relates to a kit for detecting, identifying, or quantifying tumor cells in the sample extracted from the tested sample, including a kit for detecting, identifying, or quantifying LAT2 expressed in normal cells in the sample, and a kit for detecting, identifying, or quantifying LAT1 expressed in tumor cells in the sample.

The kit for diagnosis in the present invention for the purpose of detecting, identifying, or quantifying LAT includes materials that can detect, identify, or quantify LAT. For example, it contains the labeled antibody and the like, including the steps of labeling with a labeling substance by alone or reacting with other substances that can provide detectable signals. In the kit of the present invention, both a kit for detecting, identifying, or quantifying LAT expressed in normal cells and a kit for detecting, identifying, or quantifying LAT expressed in tumor cells are one type of a kit for detecting, identifying, or quantifying LAT. A set of the same type of the kit for measurement in order to quantify LAT is preferably used but not limited to this.

For example, while a fluorescent substance labeled material can be contained in the kit for detecting, identifying, or quantifying LAT expressed in normal cells (for example, LAT2), a radioisotope labeled material can be contained in the kit for detecting, identifying, or quantifying LAT expressed in tumor cells (for example, LAT1). However, the antibody labeled with radioisotope is preferably different from the antibody labeled with a fluorescent substance with a different wavelength in the kit.

(Experimental Methods)

The effect of LAT in the present invention is further explained in detail. First of all, the present inventors reviewed an immunohistological study of LAT. Mammary gland tumor cells are extracted in a surgical procedure and a paraffin-embedded tissue specimen is prepared. The paraffin-embedded tissue specimen of mammary gland tumor cells is subjected to the steps of deparaffinizing and blocking, and treating with an anti-LAT antibody at the final concentration of 2 μg/mL (for the study of LAT1, a human anti-LAT1 mouse monoclonal antibody is used (refer to Non-Patent Literature 1, pp. 23, in FIG. 3A pp. 631), a human anti-LAT2 polyclonal rabbit antibody is used for the study of LAT2 (anti-hEST3A-N antibody, TransGenic inc., Kumamoto)) at a temperature of 4° C. overnight. After washing the specimen with PBS, a universal antibody contained in a ChemMate DAKO ENVISION System kit (DAKO ChemMate ENVISION System HRP kit) is added to the tissue specimen in either case of studying LAT1 or LAT2, and the tissue specimen is treated with the universal antibody at room temperature for 30 minutes. Then color is developed by reacting with a DAB (3,3'-diaminobenzidine tetrahydrochloride) substrate solution.

Figure 1:
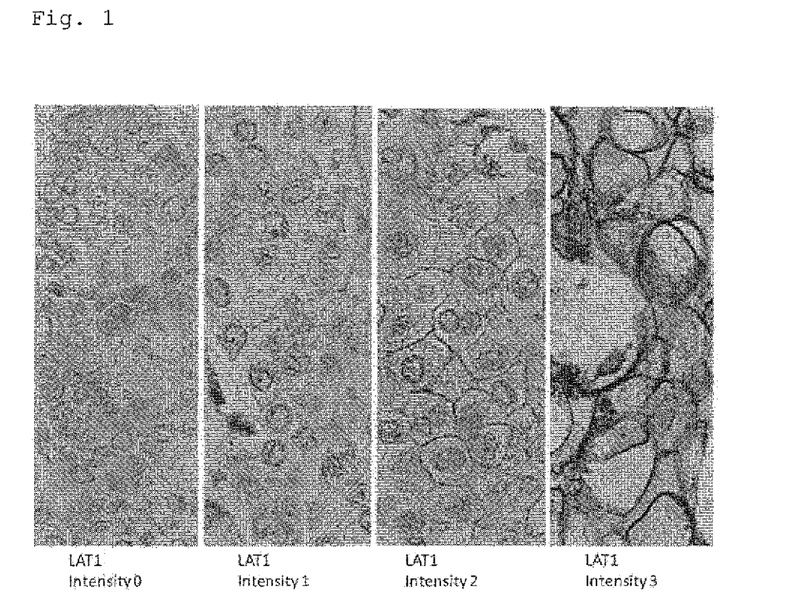
FIG. 1 shows the baseline of the intensity of LAT1 expression. The incidence of LAT1 is determined on the basis of the degree of this staining.
Figure 2:
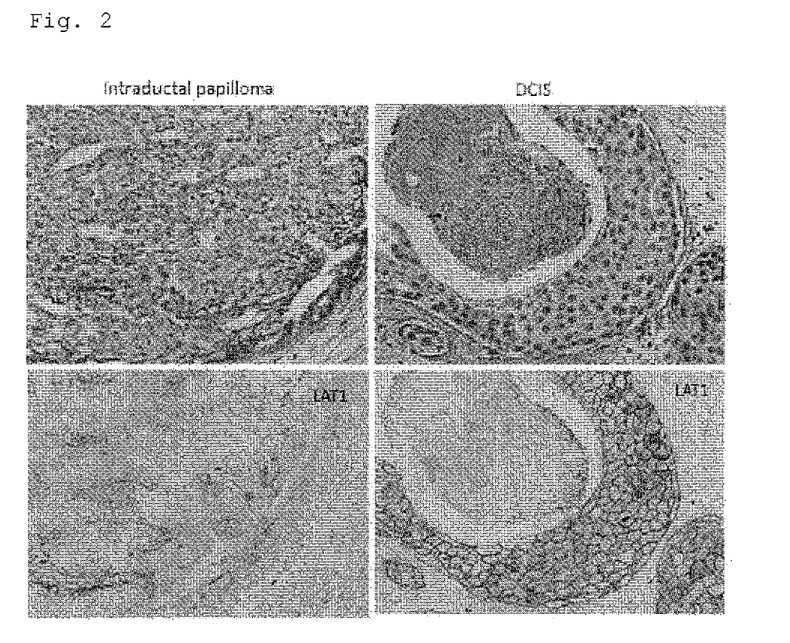
FIG. 2 shows the comparison of the expression of LAT1 between intraductal breast papilloma and ductal carcinoma in situ.
Figure 3:
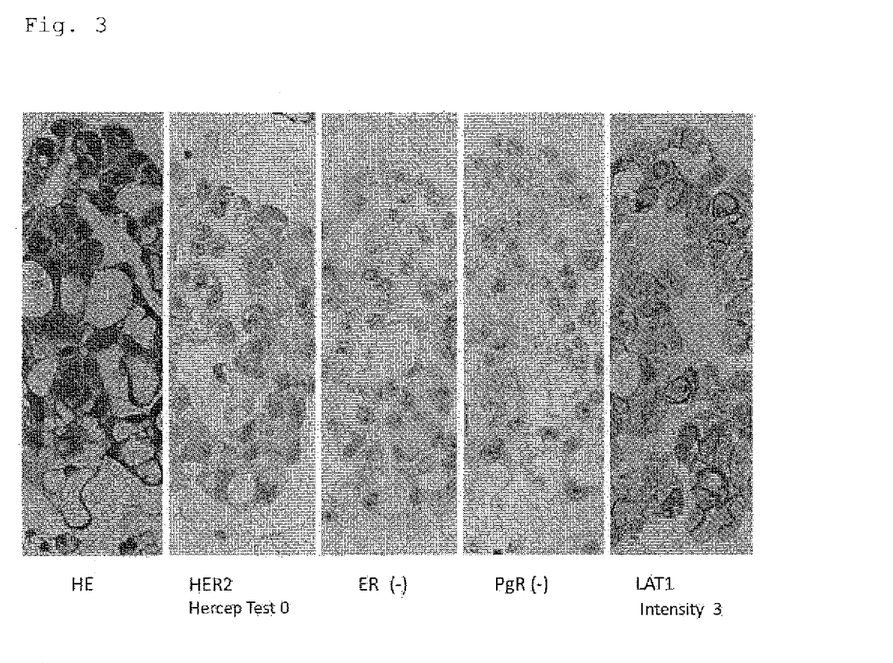
FIG. 3 shows a case that expresses LAT1 at a high level in the tissues of triple negative breast cancer that is negative for all of ER, PgR and HER2.
Figure 4:
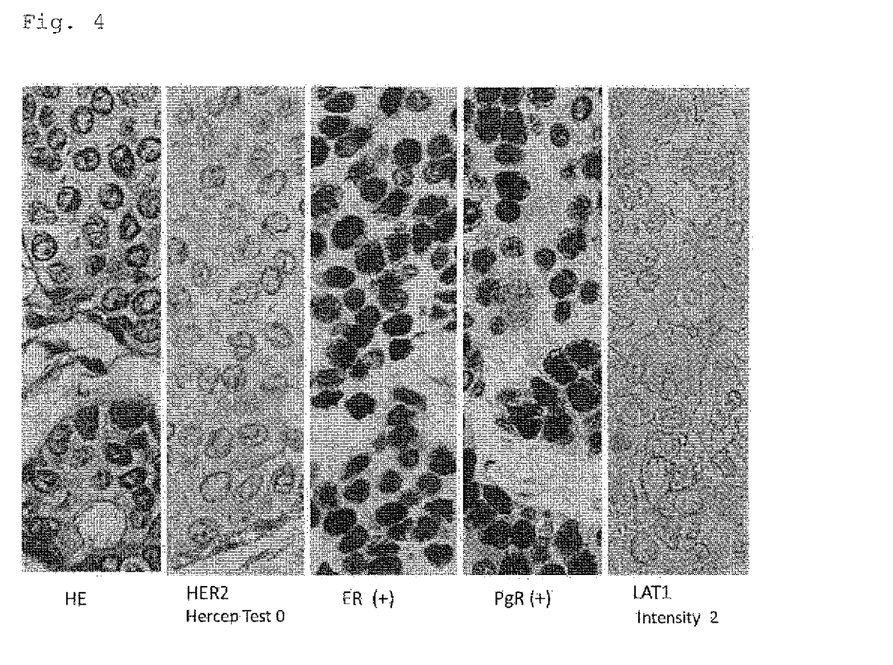
FIG. 4 shows a case that expresses LAT1 in the tissues of HER2-negative breast cancer.
Figure 5:
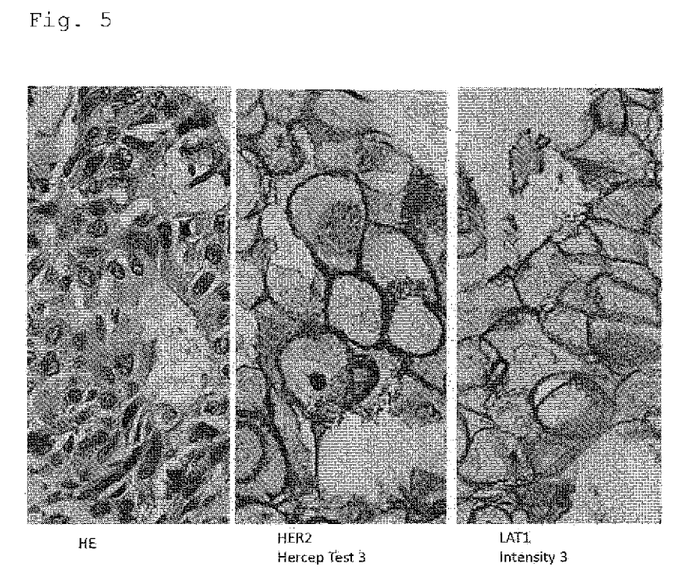
FIG. 5 shows a case that expresses LAT1 in the tissues of HER2-positive breast cancer.

As a result, while the specific staining by reacting with the LAT1 antibody was recognized in the specimen prepared from cancer cells, the specific staining by reacting with LAT2 was not found. FIGS. 1 to 5 show the results of the staining tests using the anti-LAT1 monoclonal antibody. For example, FIG. 1 shows photos indicating the baseline for the intensities of LAT1 expression, FIG. 2 shows a case expressing LAT1 in malignant ductal carcinoma in situ, FIG. 3 shows a case with the overexpression of LAT1 in triple negative breast cancer, FIG. 4 shows a case expressing LAT1 in HER2 negative breast cancer, FIG. 5 shows a case expressing LAT1 in HER2 positive breast cancer. Hereinafter, each of them is explained.

FIG. 1 shows the baseline indicating the intensities of LAT1 expression. The expression of LAT1 is obtained from a value obtained from multiplication of the intensity of expression (intensity) [0 (negative), 1 (mild positive), 2 (moderate positive), 3 (intensely positive)] and the area of expression region (area) [0 (negative), 1 (regional, the expression region is less than 10%), 2 (partial, the expression region is larger than 10% and less than 30%) and 3 (diffused, the expression region is larger than 30%)] as an evaluated value (score) by a modified method (refer to Non-Patent Literature 4) of a Sinicrope's method (refer to Non-Patent Literature 11). The incidence of LAT1 is determined on the basis of the degree of this staining. FIG. 1 indicates the intensities of LAT1 expression as reference showing the intensity 0, intensity 1, intensity 2, and intensity 3 from the left of the photo.

(Discrimination Between Malignancy and Benignancy in Intraductal Breast Tumors)

FIG. 2 shows a comparison between intraductal breast papilloma and ductal carcinoma in situ, which are both categorized in intraductal breast tumor. On the upper portion of the photo HE (hematoxylin-eosin) staining is shown, on the bottom of the photo the result of an immunostaining treated with LAT1 is shown. The upper left is a HE stained photo of intraductal breast papilloma, which is benign, and the upper right is that of ductal carcinoma in situ, which is malignant. On the left, the photo shows intraductal breast papilloma treated with the immunostaining of LAT1; on the bottom right the photo is that of ductal carcinoma in situ. As obvious in FIG. 2, while the expression of LAT1 is rarely seen in intraductal breast papilloma, the intense expression of LAT1 is observed in the cell membrane of ductal carcinoma in situ. The scores of LAT1 expression in the group of ductal carcinoma in situ are significantly higher compared to those in the group of intraductal breast papilloma. Therefore, the application of LAT1 as a biomarker enables diagnosis of intraductal breast papilloma and ductal carcinoma in situ in a simple method, for which the discrimination of those was difficult until now.

Among intraductal breast tumors, the discrimination in tissue diagnosis between intraductal breast papilloma, which is benign, and ductal carcinoma in situ, which is malignant is important and essential to judge the requirement of operational resection. However, in case a histopathological method using specimens treated with a conventional HE staining for discriminating between the two tumors, the definite elements of the discrimination are not clarified, and there are a lot of lesions where the discrimination is difficult. The present invention has found that the expression of LAT1 was extremely low in benign intraductal breast papilloma, which was a clear contrast to malignant ductal carcinoma in situ showing the expression of LAT1 at a high level. Therefore, the evaluation of the immunohistological expression of LAT1 enables the discrimination between benignancy and malignancy.

(Diagnosis of Triple Negative Breast Cancer)

FIG. 3 shows findings of the expression of LAT1 in triple negative breast cancer cells, which are negative for all of ER (estrogen receptor), PgR (progesterone receptor), and HER2. Findings in the case of HE (hematoxylin-eosin) staining (standard staining), and treated with HER2, ER, PgR, and LAT1 are shown in order from the left. This is a case showing positive to LAT1 at the intensity of 3 (high intensity) in triple negative breast cancer cells that are negative to all of ER, PgR and HER2. Since 14 out of 17 cases in the group of triple negative (about 83%) have the expression of LAT1 at a high level (score 6 or more), LAT1 is thought to be a useful biomarker for triple negative breast cancer.

Among infiltrating cancers, there was no effective a molecular-targeted therapy for triple negative breast cancers until now. However, the expression of LAT1 at a high level was recognized many in the triple negative breast cancer group. Since many patients with triple negative breast cancers have a poor prognosis clinically, this finding is consistent with the fact that patients with prostate cancer of which expression of LAT1 was at a high level had a poor prognosis compared to cases expressing LAT1 at a low level. Accordingly, it has been suggested that anti-LAT1 molecular-targeted therapy (including substances that react with anti-LAT1 antibody, LAT1 transporter, and the like) would be useful for the treatment of triple negative breast cancers, and the introduction of chemotherapy of which target is LAT1 would be expected in the future.

FIG. 4 shows a case of breast cancer with HER2 negative (score 0 in a Hercep Test) and LAT1 positive among infiltrating cancers. In order from the left, a panel shows the cases treated with ER, PgR, HER2 and LAT1. This case showed positive for ER and PgR, and negative for HER2 in the nucleus, positive (intensity 2) for LAT1 in cell membrane.

FIG. 5 shows a case of breast cancer with HER2 positive (score 3 in the Hercep Test) and LAT1 positive at a high expression among infiltrating cancers. In order from the left, the figure shows the case treated with HE (hematoxylin-eosin) staining, treated with HER2 and LAT1. As a result, a strong staining of the sample treated with the LAT1 antibody at the intensity of 3 (high intensity) was recognized in the case of HER2 positive (score 3 in the Hercep Test). Among infiltrating cancers in FIGS. 4 and 5, the scores of LAT1 expression in the group of HER2 positive cases (score 3 in the Hercep Test) were significantly higher compared to those in the group of HER2 negative cases (score 0 in the Hercep Test).

From these results, LAT1 can be a new diagnostic tool for discriminating between benignancy and malignancy of intraductal breast tumors that are difficult to diagnose until now. Moreover, LAT1 can be an extremely promising biomarker for the treatment of triple negative breast cancers, which are negative for all of ER, PrG and HER2.

EXAMPLES

Hereinafter, the present invention is specifically explained by Examples. The present invention, however, is not limited to those Examples.

Reference Example 1

Extraction of Experimental Samples

Neoplastic lesions of mammary glands, which were surgically resected between 2005 and 2009 at a facility where the present inventors belonged, were randomly extracted. Pathological samples of surgical materials in a total of 87 cases including 10 cases of intraductal breast papilloma, 10 cases of ductal carcinoma in situ (DCIS), and 67 cases of infiltrating cancer (invasive carcinoma) were used. Among them, 17 cases were triple negative infiltrating carcinomas that were negative for all of ER, PgR, and HER2.

Example 1

Staining Using an Anti-LAT Antibody

All the extracted neoplastic lesions of mammary glands in Reference Example 1 were subjected to 10% formalin fixation and a paraffin-embedded block was prepared, further prepared a thinly sliced section with a 3 μm in a thickness from a typical block having maximum divided face of neoplastic lesions. Furthermore, after activating with a microwave for 5 minutes, the sliced section was incubated with the anti-LAT1 mouse monoclonal antibody (refer to Non-Patent Literature 1 pp. 23, in FIG. 3A pp. 631) prepared by the present inventors at a temperature of 4° C. or lower overnight. Further, the section was added a universal antibody contained in a DAKO ChemMate ENVISION System HRP kit, and reacted at room temperature for 30 minutes, and then color was developed by reacting with a DAB (3,3'-diaminobenzidine tetrahydrochloride) substrate solution. For nucleus staining, methyl green or Mayer's Hematoxylin staining was carried out. For the immunostaining of ER and PgR, a Ventana XT system (Ventana Japan, Tokyo, Japan) was used, and the immunostaining of HER2 was carried out by using a DAKO EGFR pharmDx kit (Dako North America Inc., Carpinteria, Calif., USA). A human anti-LAT2 rabbit polyclonal antibody (anti-hEST3A-N antibody, TransGenic Inc., Kumamoto) was used for the immunostaining of LAT2.

As a result, the expression of LAT1 (the scores of LAT1 expression were in the range of 0 to 9) was found in many of the breast cancer cells, LAT2 was also expressed although it was mild (the scores of LAT2 expression were in the range of 0 to 3). Meanwhile, the scores of LAT1 expression in normal cells were in the range of 0 to 1, the scores for LAT2 were in the range of 1 to 4.

The expression of LAT1 was obtained from multiplication of the intensity of expression (intensity) [0 (negative), 1 (mild positive), 2 (moderate positive), 3 (intensely positive)] and the area of expression region (area) [0 (negative), 1 (regional, the expression region is less than 10%), 2 (partial, the expression region is 10% and, less than 30%) and 3 (diffused, the expression region is 30% or more)] as an evaluated value (score) by a modified method (refer to Non-Patent Literature 4) of a Sinicrope's method (refer to Non-Patent Literature 11). Statistical treatment was carried out so that the values were expressed as mean±SD in each group. The non-parametric Mann-Whitney U test was carried out to compare the two groups, and a level of significance was determined to be less than 5%.

Results

Figure 6:
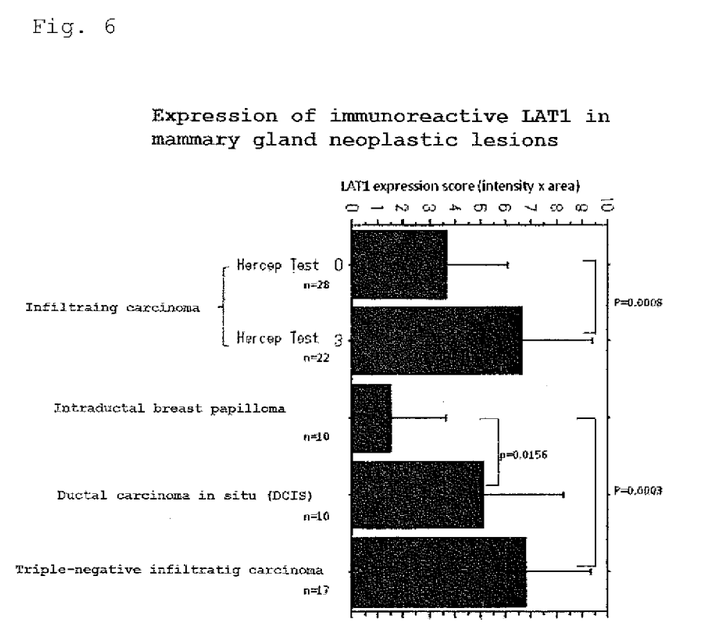
FIG. 6 shows the comparison of the expression of LAT1 in the lesions of mammary gland tumor.

The result obtained in Example 1 is shown in FIG. 6, which shows the comparison of the expression of LAT1 in mammary gland tumors.

(1) Comparison of LAT1 Expressions Between the Groups of Ductal Carcinoma In Situ and Intraductal Breast Papilloma The score of LAT1 expression in the group of ductal carcinoma in situ (DCIS), which is malignant, was significantly high (p=0.0156) indicating 5.1±3.2 compared to 1.5±2.1 in the group of intraductal breast papilloma (intraductal breast papilloma), which is benign.

(2) The Comparison of LAT1 Expressions Between Cases with HER2 Positive and Negative Among infiltrating cancers (invasive carcinoma), the score of LAT1 expression was 6.6±2.8 in the group of cases with HER2 positive (score 3 in the Hercep Test), which was significantly higher compared to 3.6±2.4 in the group of cases with HER2 negative (score 0 in the Hercep Test) ($p=0.0008$). From this result, the score of LAT1 is high in cases with HER2 positive, and it is said that the degrees of malignancy are high in terms of cell proliferation.

(3) LAT1 Expression in the Group of Triple Negative Breast Cancers

Many triple negative breast cancers, which were negative for all of the ER, PgR and HER2, were the cases with overexpressed LAT1 (14 out of 17 cases had the score 6 or more, e.g., approximately 83%), the scores of LAT1 expression in the 17 cases was 6.8±2.6 at a high level. From this result, many of triple negative breast cancers have LAT1 with a high score, and thus, the molecular-targeted therapy of which target is LAT1 seems to be effective for triple negative breast cancers.

The invention claimed is:

1. A method comprising contacting an anti-LAT1 monoclonal antibody to a mammary gland tissue extracted from a subject; and detecting, identifying, and quantifying LAT1 in the tissue, wherein the mammary gland tissue has been confirmed to be triple negative in the expression of the estrogen receptor, progesterone receptor and HER2.

2. The method according to claim 1, wherein the mammary gland tumor is intraductal breast tumor, and a degree of malignancy in the mammary gland tumor is diagnosed.

3. The method according to claim 1, further comprising contacting the mammary gland tissue with antibodies against the estrogen receptor, progesterone receptor and HER2 to confirm that the mammary gland tissue is triple negative in the expression of the estrogen receptor, progesterone receptor and HER2.

4. The method according to claim 3, wherein the mammary gland tumor is intraductal breast tumor, and a degree of malignancy in the mammary gland tumor is diagnosed.

* * * * *